United States Patent [19]

Giuliano

[11] Patent Number: 5,086,515
[45] Date of Patent: Feb. 11, 1992

[54] WELDING SHIELD APPARATUS

[76] Inventor: Samuel S. Giuliano, 258 Walzford Rd., Rochester, N.Y. 14622

[21] Appl. No.: 622,629

[22] Filed: Dec. 5, 1990

[51] Int. Cl.⁵ .................................................. A61F 9/06
[52] U.S. Cl. .................................................. 2/8
[58] Field of Search ......................... 2/7, 8, 9, 10, 422, 2/424

[56] References Cited

U.S. PATENT DOCUMENTS

| | | | |
|---|---|---|---|
| 2,461,605 | 2/1949 | Huntsman | 2/8 |
| 2,668,951 | 2/1954 | MacLean | 2/8 |
| 2,729,820 | 1/1956 | Anderson | 2/8 |
| 2,731,637 | 1/1956 | Kaplan et al. | 2/9 |
| 2,736,027 | 2/1956 | Parmelee | 2/8 |
| 2,747,191 | 5/1956 | Hoffmaster | 2/8 |
| 2,755,476 | 7/1956 | Bowers, Sr. | 2/8 |
| 2,758,307 | 8/1956 | Treiber | 2/9 |
| 2,915,756 | 12/1959 | Rex et al. | 2/8 |
| 3,090,046 | 5/1963 | Bowers, Sr. | 2/8 |
| 3,380,073 | 4/1968 | McLaughlin | 2/10 |
| 3,582,991 | 6/1971 | Metz | 2/8 |
| 3,868,727 | 3/1975 | Paschall | 2/8 |
| 4,539,713 | 9/1985 | Hodge | 2/8 |
| 4,646,363 | 3/1987 | Wood | 2/8 |
| 4,649,571 | 3/1987 | Falkiner | 2/8 |

FOREIGN PATENT DOCUMENTS 2220977 11/1974 France ............................. 2/8

Primary Examiner—Werner H. Schroeder
Assistant Examiner—Michael A. Neas
Attorney, Agent, or Firm—Leon Gilden

[57] ABSTRACT

An welding shield is provided to include an adjustable, horizontal cylindrical band mounting diametrically thereof a vertical semi-cylindrical band. The horizontal band mounts a plurality of shields, including an opaque and clear shield for use of the shield in welding and grinding operations respectively. Each shield includes a plurality of ears, wherein the ears each include an ear aperture, wherein each ear aperture is coaxially aligned and mounted to the horizontal cylindrical band by way of an elongate threaded fastener, wherein each of the threaded fasteners is coaxially aligned relative to one another. The fasteners each include an elongate, cylindrical shank mounting a frictional spring between the spring and the shields, and wherein each of the fasteners also includes a thumb screw member to provide selective frictional securement of each of the fasteners to the band structure for selective frictional retention of the shield as required. Further, an attachment plate is provided for selective securement to the band for selective replacement of the shields.

1 Claim, 4 Drawing Sheets

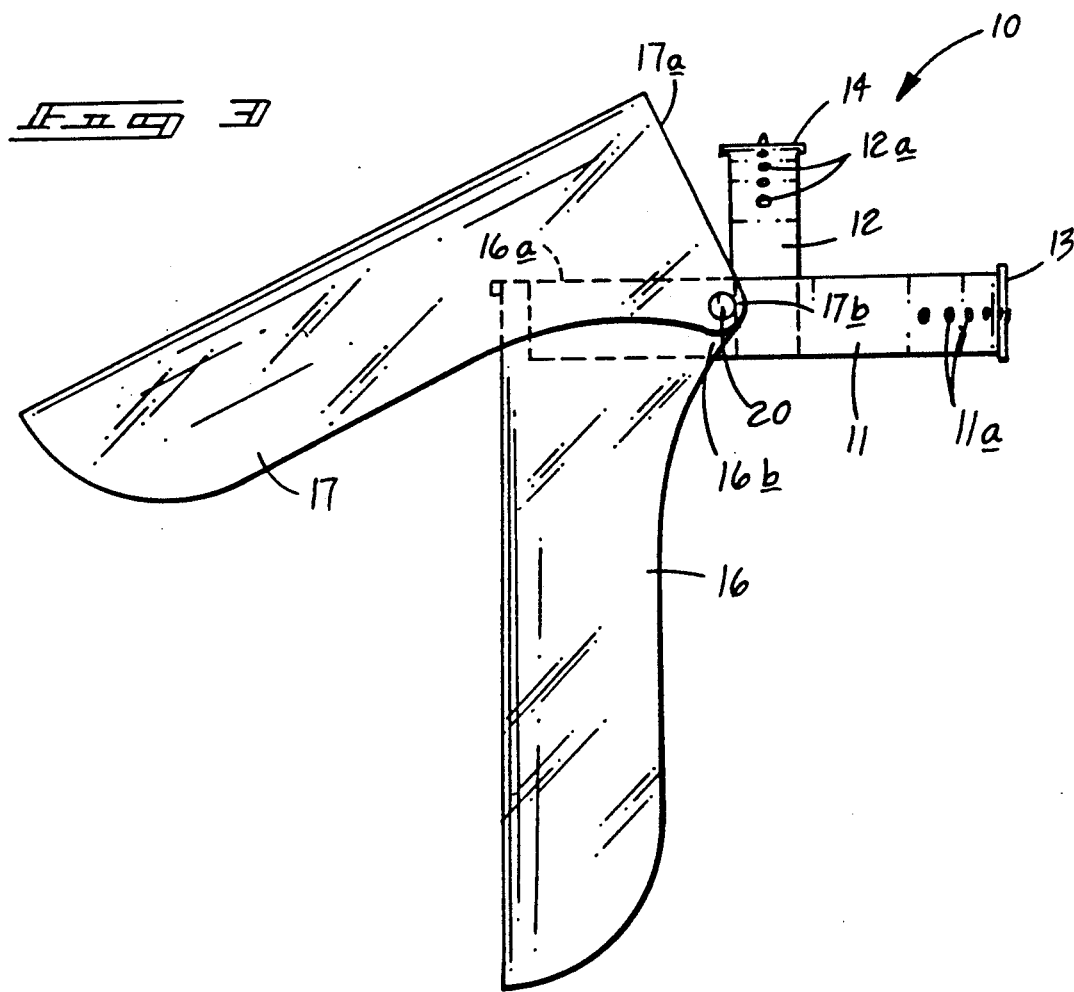
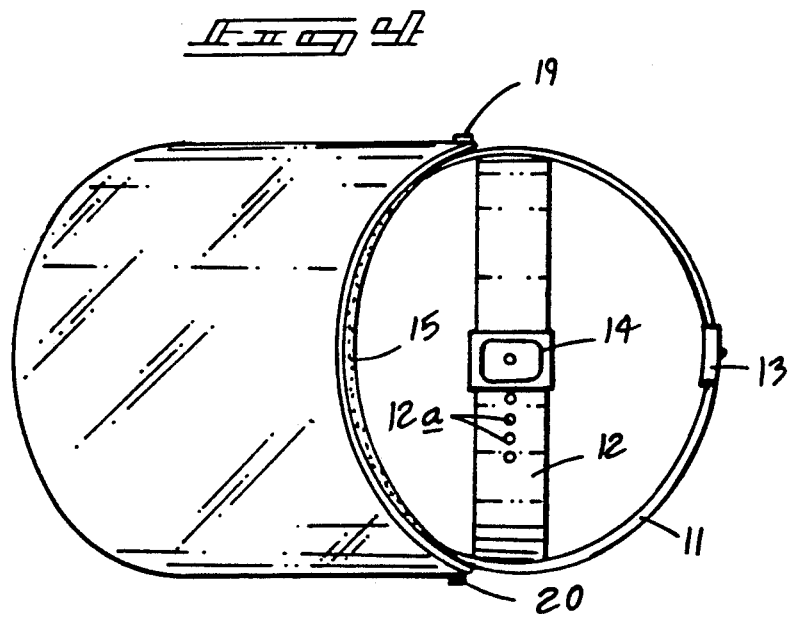

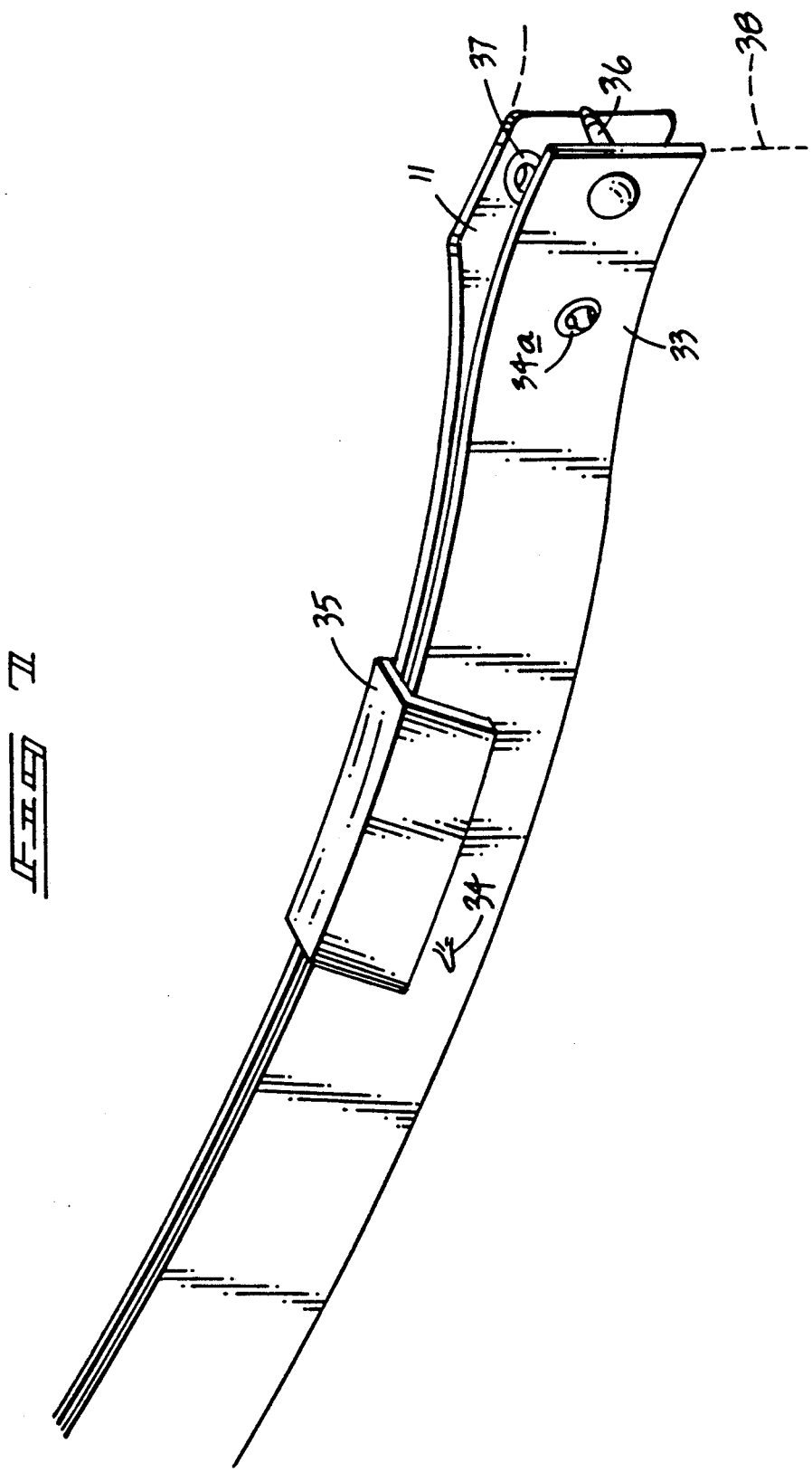

WELDING SHIELD APPARATUS

BACKGROUND OF THE INVENTION

1. Field of the Invention

The field of invention relates to welding masks, and more particularly pertains to a new and improved welding shield apparatus wherein the same provides for selective application of various shields in various metal working operations.

2. Description of the Prior Art

Welding shields of various types have been utilized in the prior art to afford facial protection during welding, as well as other operations. Such prior art is exemplified in U.S. Pat. No. 3,582,991 to Metz wherein a welding shield structure utilizes a transparent or clear grinding mask at one end of the mask structure, and a pivotally mounted welding type opaque shield at an opposed end of the mask structure.

U.S. Pat. No. 4,646,363 to Wood sets forth a welding helmet, wherein the welding helmet utilizes a plurality of visor elements of opaque and clear construction to permit use of the shield for welding and general viewing.

U.S. Pat. No. 4,649,571 to Falkiner sets forth a welding helmet fitted with a plurality of lenses, one tinted and one relatively clear mounted at various positions through the forward face of the shield.

U.S. Pat. No. 4,539,713 to Hodge sets forth a chin operated welding hood to permit selective pivotment of a face shield overlying an initial face shield.

As such, it may be appreciated that there continues to be a need for a new and improved welding shield apparatus as set forth by the instant invention which addresses both the problems of ease of use as well as compactness in construction and in this respect, the present invention substantially fulfills this need.

SUMMARY OF THE INVENTION

In view of the foregoing disadvantages inherent in the known types of welding shield apparatus now present in the prior art, the present invention provides a welding shield apparatus wherein the same provides for a plurality of shields pivotally mounted to a horizontal cylindrical mounting band. As such, the general purpose of the present invention, which will be described subsequently in greater detail, is to provide a new and improved welding shield apparatus which has all the advantages of the prior art welding shield apparatus and none of the disadvantages.

To attain this, the present invention provides a welding shield including an adjustable, horizontal cylindrical band mounting diametrically thereof a vertical semi-cylindrical band. The horizontal band mounts a plurality of shields, including an opaque and clear shield for use of the shield in welding and grinding operations respectively. Each shield includes a plurality of ears, wherein the ears each include an ear aperture, wherein each ear aperture is coaxially aligned and mounted to the horizontal cylindrical band by way of an elongate threaded fastener, wherein each of the threaded fasteners is coaxially aligned relative to one another. The fasteners each include an elongate, cylindrical shank mounting a frictional spring between the spring and the shields, and wherein each of the fasteners also includes a thumb screw member to provide selective frictional securement of each of the fasteners to the band structure for selective frictional retention of the shields as required. Further, an attachment plate is provided for selective securement to the band for selective replacement of the shields.

The invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved welding shield apparatus which has all the advantages of the prior art welding shield apparatus and none of the disadvantages.

It is another object of the present invention to provide a new and improved welding shield apparatus which may be easily and efficiently manufactured and marketed.

It is a further object of the present invention to provide a new and improved welding shield apparatus which is of a durable and reliable construction.

An even further object of the present invention is to provide a new and improved welding shield apparatus which is susceptible of a low cost of manufacture with regard to both materials and labor, and which accordingly is then susceptible of low prices of sale to the consuming public, thereby making such welding shield apparatus economically available to the buying public.

Still yet another object of the present invention is to provide a new and improved welding shield apparatus which provides in the apparatuses and methods of the prior art some of the advantages thereof, while simultaneously overcoming some of the disadvantages normally associated therewith.

Still another object of the present invention is to provide a new and improved welding shield apparatus wherein the same is arranged to permit manual displacement and positioning of an opaque shield relative to a clear shield, wherein the opaque shield is of a generally tinted construction such as green typically utilized in welding operations.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic side view, taken in elevation, of the instant invention.

FIG. 4 is an orthographic top view of the instant invention.

FIG. 7 is an isometric illustration of the attachment plate in association with the mounting band of the instant invention.

DESCRIPTION OF THE PREFERRED EMBODIMENT

Figure 1:
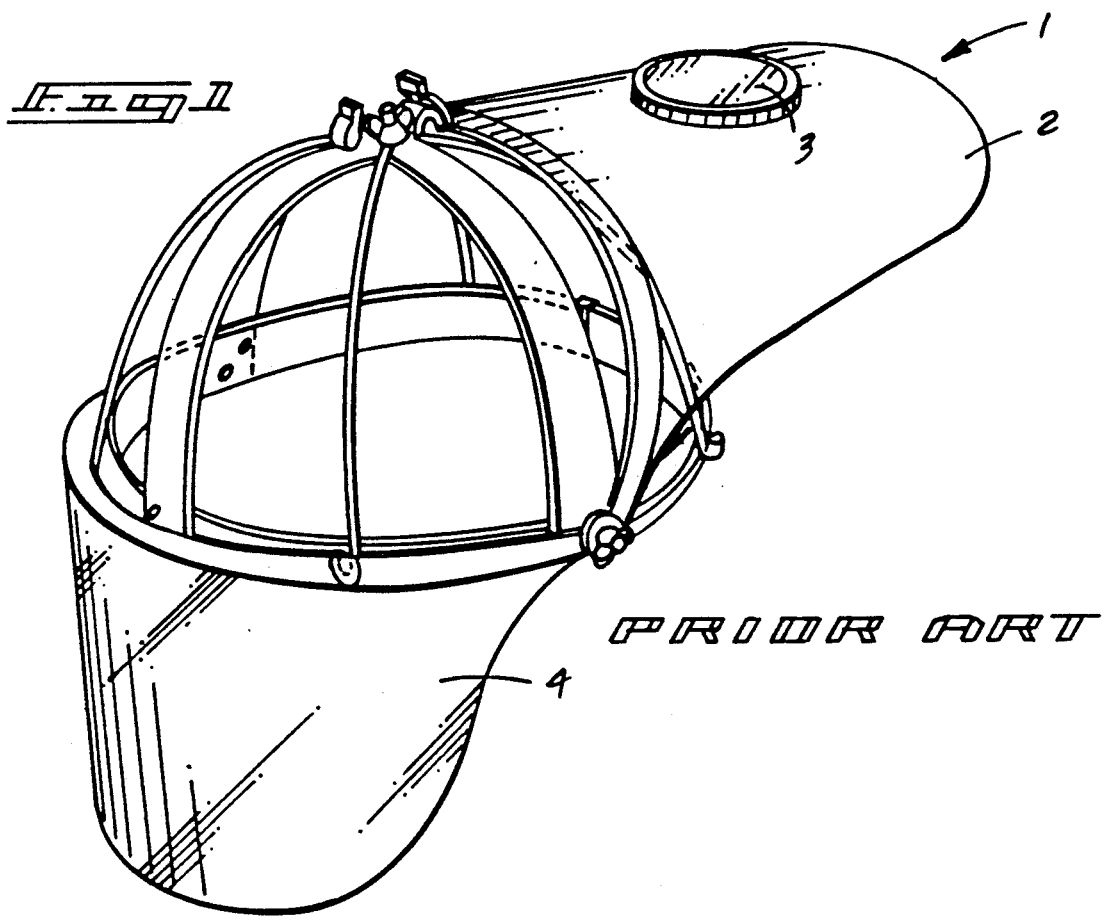
FIG. 1 is an isometric illustration of a prior art welding shield apparatus.
Figure 2:
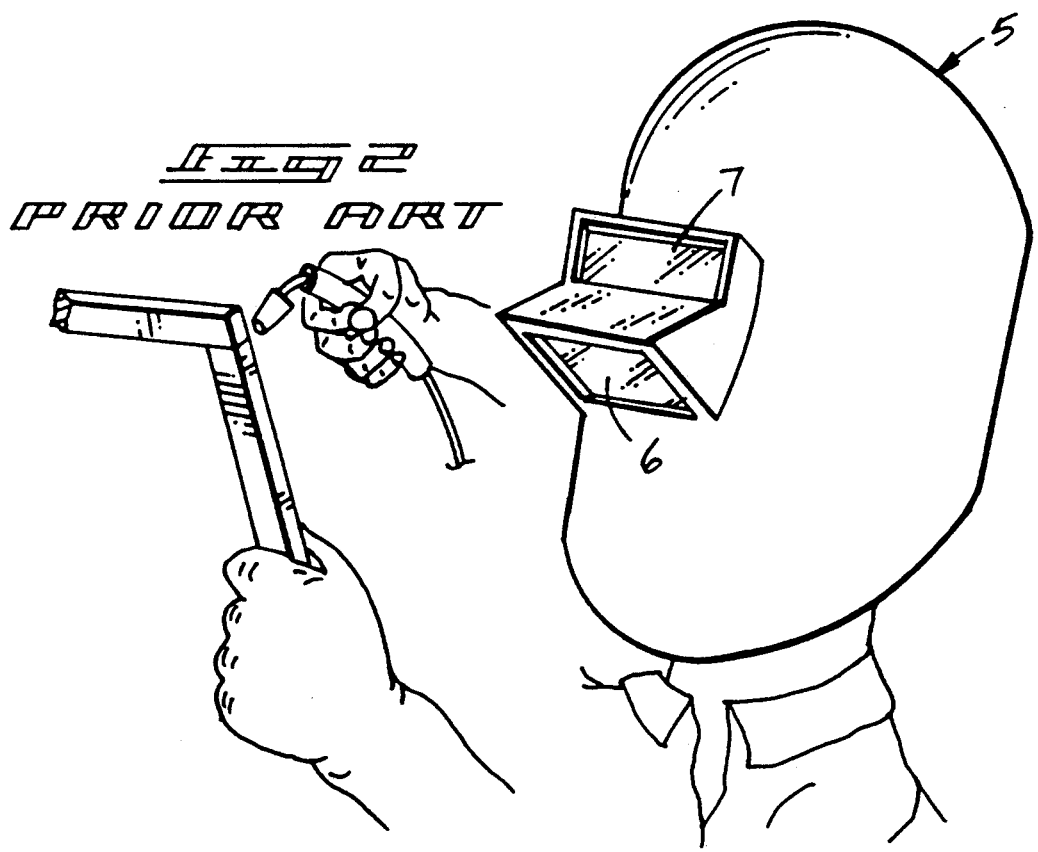
FIG. 2 is a further example of a prior art welding shield apparatus.
Figure 5:
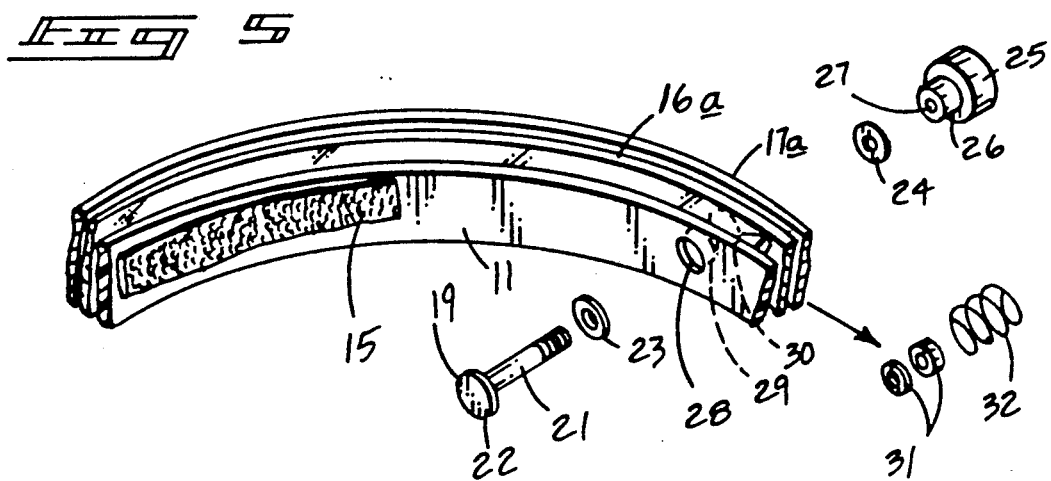
FIG. 5 is an isometric enlarged illustration of the mounting band of the instant invention.

With reference now to the drawings, and in particular to FIGS. 1 to 7 thereof, a new and improved welding shield apparatus embodying the principles and concepts of the present invention and generally designated by the reference numeral 10 will be described.

FIG. 1 illustrates a prior art welding and grinder shield organization 1, wherein a transparent grinding shield 4 is mounted to the annular band directed in a first direction, with a second shield 2 of an opaque construction utilizing a light filtering glass 3 mounted medially thereof, as set forth in U.S. Pat. No. 3,582,991. The shield construction 5, as set forth in FIG. 2, utilizes a transparent viewing lens 6, with an overlying opaque lens 7 fixedly mounted within a forward face of the mask structure, as set forth in U.S. Pat. No. 4,646,363.

More specifically, the welding shield apparatus 10 of the instant invention essentially comprises a horizontal, cylindrical mounting band 11, including a series of first apertures 11a cooperative with a first adjustment buckle or finger ratchet 13 to permit circumferential adjustment of the horizontal mounting band. A vertical semi-cylindrical mounting band is fixedly mounted diametrically to and directed upwardly of an orthogonal relationship to the horizontal cylindrical mounting band, and includes a second series of apertures 12a cooperative with a second adjustment buckle 14. A fluid absorbent band member 15 is fixedly mounted to an interior surface of the horizontal mounting band 11 intermediate of the mounting of the vertical semicylindrical band 12. The fluid absorbent band member 15 functions as a perspiration absorbent member during wearing of the organization about the head of an individual in a conventional manner.

A clear shield 16, including an upper arcuate edge 16a aligned with an upper edge of the horizontal mounting band when the clear shield 16 is in a first lowered position orthogonally oriented to the horizontal mounting band, is pivotally mounted to the horizontal mounting band. Similarly, an opaque or tinted shield 17 includes a second arcuate edge 17a that is aligned with the first arcuate edge 16a when the opaque shield 17 is in a first lowered position and is spaced above the horizontal mounting band 11 when the opaque shield is in a raised position. Similarly, the clear shield 16 is raised to a second position selectively by an individual. Each shield 16 and 17 includes a plurality of respective first and second ears 16b and 17b. The first and second ears each include a respective second and third bore 29 and 30 (see FIG. 5) that is aligned with a first bore 28 that is directed through the horizontal mounting band 11. A fastener pivotally secures each ear of the first and second ears 16b and 17b of the clear and opaque shields 16 and 17 respectively to the horizontal mounting band 11. As illustrated in FIG. 4, a right and left friction fastener 19 and 20 is utilized in this respect. Each fastener of the right and left friction fasteners includes a threaded fastener shaft 21, with a planar fastener head 22 mounted at an upper terminal end thereof. The planar head minimized contact with an individual mounting the band 11. The fastener shaft 21 is directed through the first, second, and third bores 28, 29, and 30 of the respective horizontal mounting band 11, clear shield 16 and opaque shield 17. A first doughnut shaped washer 23 is positioned between the planar head 22 and an interior surface of the horizontal mounting band 11. A second doughnut shaped washer 24 is mounted between an exterior surface of each second ear 17b and a cylindrical handle 25 defined by a first diameter mounting a cylindrical shank 26 of a second diameter less than that of the first diameter. The cylindrical handle 25 permits manual rotation of the handle and provides for adjustable frictional grasping and retention of each shield relative to the horizontal mounting band. A plurality of third spacer washers 31 are positioned between the exterior surface of the horizontal cylindrical mounting band 11 and the clear shield 16, with a spring member 32 interposed about the third spacer washers 31 to provide frictional biasing of the components of each friction fastener 19 or 20 to maintain adjustment of the cylindrical shank 26 and its threaded bore 27 receiving a forward terminal end of the threaded fastener shaft 21 directed through the exterior second ear 17b and associated third bore 30 as illustrated. For purposes of illustration, it is noted that only one of the friction fastener members has been described, but it is understood that right and left friction fasteners 19 and 20 are of identical construction.

Figure 6:
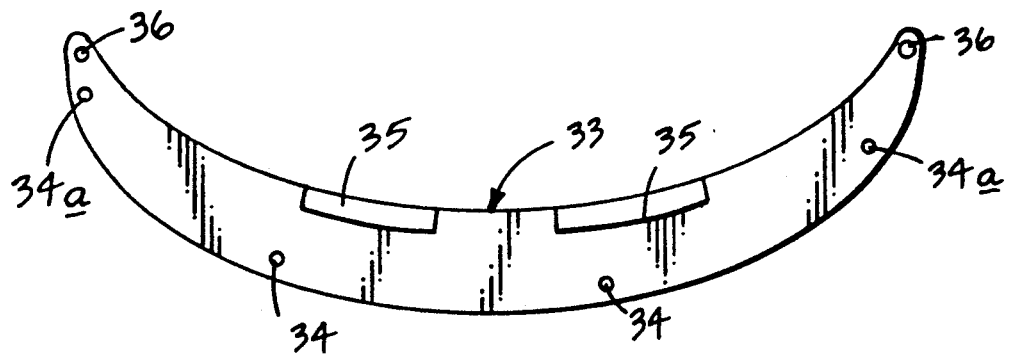
FIG. 6 is an orthographic frontal view of an attachment plate utilized by the instant invention.

FIGS. 6 and 7 illustrate the use of an arcuate attachment plate 33 that is selectively mounted to a forward or exterior surface of the mounting band 11 to permit selective attachment of additional shields thereto. The arcuate attachment plate 33 includes a plurality of positioning studs 34 extending exteriorly thereof that are received within recesses of associated shield members that are attached to an exterior surface of the attachment plate 33. The positioning studs 34 cooperate with snap fastener mountings 34a to receive such shield structure. A plurality of flexible "U" shaped tabs 35 are arranged to secure the arcuate attachment plate 33 to the forward surface of the horizontal cylindrical mounting band 11. A snap fastener stud 36 is provided each end of the attachment plate 33 for reception within an associated fastener receiving bore 37 of the band 11. Additional shields 38 are thereby selectively secured to the forward surface of the band 11 and provide selective attachment of additional shield structures 38, as illustrated.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A welding shield apparatus including a support, wherein the support is arranged for defining an open cavity, the support including a horizontal adjustable cylindrical mounting band, including a first adjustment member to provide annular adjustment of the horizontal mounting band, and a vertical semi-cylindrical mounting band orthogonally mounted to the horizontal mounting band by first mounting means, with the vertical mounting band including a second adjustment member to effect adjustment of the second mounting band, and a first clear shield mounted to the horizontal cylindrical mounting band forwardly of the vertical semi-cylindrical mounting band, with the first adjustment member mounted rearwardly of the vertical semi-cylindrical band on the horizontal cylindrical mounting band, and an opaque shield mounted coextensively with and overlying the clear shield, the clear shield and the opaque shield pivotally mounted to the horizontal cylindrical mounting band forwardly of the vertical semi-cylindrical mounting band, and wherein the clear shield includes a first upper arcuate edge, with a plurality of first ears extending rearwardly of the clear shield along the first upper arcuate edge, and the opaque shield including a second upper arcuate edge, with the opaque shield including a plurality of second ears, wherein the second ears extend rearwardly of the opaque shield along the second upper arcuate edge, and the first upper arcuate edge and the second upper arcuate edge are aligned relative to one another in a lowered position and aligned with an upper edge of the horizontal cylindrical mounting band in the lowered position, wherein the clear shield and opaque shield are arranged orthogonally relative to the horizontal cylindrical mounting band in the lowered position, and wherein the first ears and the second ears each include respective second apertures and third apertures, wherein the second apertures and third apertures are coaxially aligned relative to one another, and the horizontal cylindrical mounting band includes a first aperture aligned with each of the second apertures and third apertures, and a fastener member directed through each of the first, second, and third apertures, and wherein the fastener member includes a threaded shank extending through the first, second, and third apertures, and the threaded shank including a planar head member positioned interiorly of the horizontal cylindrical mounting band, and a first washer mounted between the planar head and the horizontal cylindrical mounting band, and a manual rotatably cylindrical handle mounted to the threaded shank exteriorly of the opaque shield, and the cylindrical handle including a threaded bore, wherein the threaded bore complementarily receives the threaded shank therewithin, and a further washer member interposed between the horizontal cylindrical mounting band and the clear shield, and a spring member mounted in surrounding relationship relative to the further washer and the horizontal cylindrical mounting band and the clear shield, and including a fluid absorbent band member mounted interiorly of the horizontal cylindrical mounting band by second mounting means, and including an arcuate attachment plate selectively securable to an exterior surface of the horizontal cylindrical mounting band, and the arcuate attachment plate includes a plurality of positioning studs, wherein the positioning studs complementarily receive a plurality of additional shield members in alignment thereon, and the attachment plate further includes a plurality of snap fasteners, wherein the snap fasteners are selectively securable to snap fastener receving bores directed through the horizontal cylindrical mounting band, and the arcuate attachment plate further includes a plurality of flexible "U" shaped tabs each receiving the arcuate attachment plate and the horizontal mounting band therewithin to assist in providing securement of the attachment plate to the horizontal cylindrical mounting band.

* * * * *